United States Patent [19]

Patel

[11] 4,418,021
[45] Nov. 29, 1983

[54] N-ISOPROPYLCARBANILYLMETHYL DITHIOPHOSPHATES

[75] Inventor: Natu R. Patel, Overland Park, Kans.

[73] Assignee: Gulf Oil Corporation, Pittsburgh, Pa.

[21] Appl. No.: 301,886

[22] Filed: Sep. 11, 1981

Related U.S. Application Data

[60] Continuation of Ser. No. 145,943, May 2, 1980, abandoned, which is a division of Ser. No. 815,335, Jul. 13, 1977, abandoned.

[51] Int. Cl.³ .................. C07F 9/165; A01N 57/14
[52] U.S. Cl. ............................. 260/943; 71/87; 424/211
[58] Field of Search .......................... 260/943, 947

[56] References Cited

U.S. PATENT DOCUMENTS 4,278,461 7/1981 Salbeck et al. .................. 260/943

Primary Examiner—Anton H. Sutto
Attorney, Agent, or Firm—Deane E. Keith; Forrest D. Stine

[57] ABSTRACT

A class of compounds having the structural formula

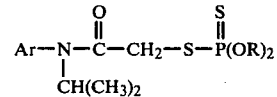

in which Ar is substituted phenyl and R is methyl or ethyl possesses improved activity as pre-emergent herbicides and insecticides.

2 Claims, No Drawings

N-ISOPROPYLCARBANILYLMETHYL DITHIOPHOSPHATES

This is a continuation of application Ser. No. 145,943, filed May 2, 1980 which is a division of application Ser. No. 815,335, filed July 13, 1977, both now abandoned.

DESCRIPTION OF THE INVENTION

N-Alkylcarbanilylmethyl dithiophosphates have been previously disclosed as pre-emergent herbicides, for example in U.S. Pat. No. 3,102,019. The one N-isopropyl compound disclosed in the aforementioned patent was inferior to the corresponding N-methyl compound as a herbicide. I have discovered, however, that the isopropyl group confers greatly increased biological activity on a small class of substituted phenyl compounds, a property of critical importance in the use of these compounds as pre-emergent herbicides and soil insecticides.

Briefly, the new class of highly effective insecticides and pre-emergent herbicides are compounds having the structural formula

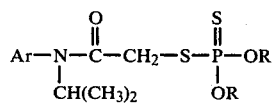

in which Ar is 3,5-dichlorophenyl, 3,4-dichlorophenyl, p-fluorophenyl, m-fluorophenyl, p-trifluoromethylphenyl, p-nitrophenyl, 4-chloro-2-methylphenyl or p-chlorophenyl and the R groups are methyl or ethyl. In general, compounds in which R is methyl are more effective as insecticides and those in which R is ethyl are more effective as pre-emergent herbicides.

a. Preparation of the Pesticides

The synthesis of N-isopropylanilines with different substituents on the aromatic ring may be carried out by the known procedure, *J. Org. Chem. V.* 24, 1551(1959). Another procedure may also be used in which reductive condensation between anilines and acetone is carried out in acetic acid with sodium borohydride, *J. Am. Chem. Soc., V.* 96, 7812(1974). However, modification of the latter procedure is necessary for the manufacture of substantial quantities. After synthesis by one of these procedures, the N-isopropylanilines are allowed to react with chloroacetyl chloride and the resulting chloroacetanilides on reaction with inorganic salts of dialkyl dithiophosphates give the desired compounds. The procedures described below illustrate the synthesis of these compounds. All of these compounds were satisfactorily identified by means of infrared and nuclear magnetic resonance spectra. All the N-isopropylanilines were purified by distillation. The dithiophosphates were obtained in the form of a syrup which was not subjected to distillation or other purification steps. In some instances, crystallization occurred on standing for a period of time. The melting points of these substances were determined.

4-Fluoro-N-isopropylaniline

A solution of 22.2 g (0.2 m) 4-fluoroaniline, and 17.6 ml (0.24 m) acetone in 120 ml (2 m) glacial acetic acid in the three neck 500 ml round bottom flask was stirred mechanically and cooled to approximately 10° C. in an ice bath. To this solution 9.4 g (0.25 m) sodium borohydride was added in parts while keeping the temperature below 20° C. It was allowed to stir at 20° C. for 30 minutes and one hour at room temperature. The mixture was poured into 500 ml ice water. The aqueous solution was made alkaline by dropwise addition of 120 ml 50% aqueous sodium hydroxide solution below 25° C. The product was extracted with hexane, (2×100 ml) which was washed with saturated sodium chloride solution, dried on anhydrous magnesium sulfate and evaporated to give a clear liquid. The product was distilled to give a clear colorless liquid product, 21.8 g B.P. 40°/0.5 mm. Yield 71%.

N-chloroacetyl-4-fluoro-N-isopropylaniline

To 100 ml dry toluene 15.3 g (0.1 m) 4-fluoro-N-isopropylaniline and 8.7 ml (0.11 m) pyridine were added and stirred. To this solution 12.4 g (0.11 m) chloroacetyl chloride was added dropwise below 25° C. It was allowed to stir overnight at room temperature and the mixture was washed with 2×100 ml water. The organic layer was dried on anhydrous magnesium sulfate and evaporated to give 22.2 g pale yellow liquid, yield 97%.

O,O-Diethyl S-(N-isopropyl-4-fluorophenylcarbamoylmethyl)dithiophosphate

To 75 ml dry acetone, 4.6 g (0.02 m) N-chloroacetyl-4-fluoro-N-isopropylaniline and 2.8 g (0.02 m) anhydrous powdered potassium carbonate were added and stirred. To this solution a solution of 4.2 g (0.02 m) diethyldithiophosphate in 25 ml dry acetone was added dropwise. It was stirred at room temperature overnight and refluxed for 2 hours. The reaction mixture was cooled to room temperature and evaporated to dryness. The residue was stirred in approximately 100 ml water and the product was extracted with two 75 ml portions of ethyl acetate. The ethyl acetate extract was dried and evaporated to low volume to give 5.5 g of amber colored syrup, yield 72%. Compounds which were made by means of the illustrated procedures are listed below.

Compounds of the formula

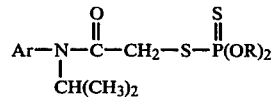

| Compound No. | Ar | R | Phys. Properties |
|---|---|---|---|
| 1 | 3,4-dichlorophenyl | ethyl | m.p. 59–60° C. |
| 2 | p-fluorophenyl | ethyl | syrup |
| 3 | p-chlorophenyl | ethyl | m.p. 48–49° C. |
| 4 | p-nitrophenyl | ethyl | m.p. 55–57° C. |
| 5 | p-chlorophenyl | methyl | syrup |
| 6 | 3,5-dichlorophenyl | methyl | syrup |
| 7 | 3,4-dichlorophenyl | methyl | syrup |
| 8 | p-nitrophenyl | methyl | syrup |
| 9 | p-fluorophenyl | methyl | syrup |
| 10 | 4-chloro-2-methylphenyl | methyl | syrup |
| 11 | 4-chloro-2-methylphenyl | ethyl | syrup |
| 12 | p-trifluoromethylphenyl | methyl | syrup |
| 13 | p-trifluoromethylphenyl | ethyl | syrup |
| 14 | m-fluorophenyl | ethyl | syrup |
| 15 | m-fluorophenyl | methyl | syrup | b. Use of the Compounds as Pre-Emergent Herbicides

There is described below an illustrative procedure for use of the pesticides of this invention as pre-emergent herbicides.

A solution of each active compound was prepared by dissolving 290 mg of the compound to be tested in 200 ml of acetone. Disposable paper trays about 2½ inches deep were filled with soil and sprayed with the acetone solution at rates of 3 lb and 1 lb of active chemical per acre of sprayed area, were seeded with 24 species of plant seeds and were then covered with about ¼ inch of soil. The plant species employed in the test are listed below.

| Common Name | Scientific Name |
| --- | --- |
| cocklebur | *Xanthium pensylvanicum* |
| lambsquarters | *Chenopodium album* |
| morning glory | *Ipomoea purpurea* |
| pigweed | *Amaranthus retroflexus* |
| wild buckwheat | *Polygonum Convolvulus* |
| wild mustard | *Brassica kaber* |
| barnyard grass | *Echinochloa crusgalli* |
| crabgrass | *Digitaria sanguinalis* |
| downy brome | *Bromus inermis* |
| giant foxtail | *Setaria faberii* |
| green foxtail | *Setaria viridis* |
| nutsedge | *Cyperus esculentus* |
| shattercane | *Sorghum bicolor* |
| wild oats | *Avena fatua* |
| alfalfa | *Medicago sativa* |
| cotton | *Gossypium herbaceum* |
| peanut | *Arachis hypogaea* |
| soybean | *Soja max* |
| sugar beets | *Beta vulgaris* |
| tomato | *Lycopersicum esculentum* |
| corn | *Zea mays* |
| grain sorghum | *Sorghum vulgare* |
| rice | *Oryza sativa* |
| wheat | *Triticum aestivum* |

Twenty-one days after seeding and treatment the plantings were examined and herbicidal effect was rated according to the schedule below.

DEGREE OF EFFECT

0 = no effect
1 = slight effect (not permanent)
2 = moderate effect (some permanent injury)
3 = severe effect (some plants died)
4 = maximum effect (all plants died)

Results obtained on representative compounds by means of the procedure described above are set forth in the following table.

| | Pre-Emergent Use at 3 lb and 1 lb per acre | | | | | | | | | | | | | | | | | | |
| --- | --- | --- | --- | --- | --- | --- | --- | --- | --- | --- | --- | --- | --- | --- | --- | --- | --- | --- | --- |
| | Compound No. | | | | | | | | | | | | | | | | | | |
| | 1 | | 2 | | 3 | | 4 | | 7 | | 6 | | 10 | | 12 | | 14 | | 15 | |
| Species | 3 lb | 1 lb | 3 lb | 1 lb | 3 lb | 1 lb | 3 lb | 1 lb | 3 lb | 1 lb | 3 lb | 1 lb | 3 lb | 1 lb | 3 lb | 1 lb | 3 lb | 1 lb | 3 lb | 1 lb |
| Cocklebur | 1 | 0 | 0 | 0 | 0 | 0 | 0 | 0 | 0 | 0 | 0 | 0 | 0 | 0 | 0 | 0 | 0 | 0 | 0 | 0 |
| Lambsquarters | 4 | 4 | 4 | 4 | 4 | 4 | 4 | 4 | 4 | 4 | 4 | 4 | 4 | 2 | 4 | 4 | 4 | 4 | 4 | 4 |
| Morning Glory | 4 | 4 | 4 | 4 | 4 | 4 | 1 | 0 | 4 | 3 | 0 | 0 | 0 | 0 | 1 | 0 | 4 | 3 | 4 | 2 |
| Pigweed | 4 | 4 | 4 | 4 | 4 | 4 | 4 | 4 | 4 | 4 | 4 | 4 | 4 | 0 | 4 | 4 | 4 | 4 | 4 | 4 |
| Wild Buckwheat | 4 | 1 | 3 | 2 | 4 | 2 | 3 | 1 | 3 | 0 | 0 | 0 | 3 | 1 | 2 | 3 | 1 | 0 | 2 | 0 |
| Wild Mustard | 4 | 4 | 4 | 3 | 4 | 4 | 4 | 4 | 4 | 4 | 4 | 4 | 3 | 2 | 4 | 3 | 2 | 1 | 4 | 1 |
| Barnyard Grass | 4 | 4 | 4 | 4 | 4 | 4 | 4 | 4 | 4 | 4 | 4 | 4 | 4 | 4 | 4 | 4 | 4 | 4 | 4 | 4 |
| Crabgrass | 4 | 4 | 4 | 4 | 4 | 4 | 4 | 4 | 4 | 4 | 4 | 4 | 4 | 2 | 4 | 4 | 4 | 4 | 4 | 4 |
| Downy Brome | 4 | 3 | 4 | 4 | 4 | 3 | 4 | 4 | 3 | 3 | 0 | 0 | 3 | 1 | 3 | 2 | 2 | 2 | 1 | 0 |
| Giant Foxtail | 4 | 4 | 4 | 4 | 4 | 4 | 4 | 4 | 4 | 4 | 4 | 4 | 4 | 2 | 4 | 4 | 4 | 4 | 4 | 4 |
| Green Foxtail | 4 | 4 | 4 | 4 | 4 | 4 | 4 | 4 | 4 | 4 | 4 | 4 | 4 | 3 | 4 | 4 | 4 | 4 | 4 | 4 |
| Nutsedge | 0 | 0 | 2 | 1 | 0 | 0 | 0 | 0 | 0 | 0 | 0 | 0 | 0 | 0 | 0 | 0 | 0 | 0 | 0 | 0 |
| Shattercane | 4 | 4 | 4 | 4 | 4 | 4 | 4 | 4 | 4 | 4 | 3 | 0 | 0 | 4 | 3 | 4 | 4 | 4 | 4 | 3 |
| Wild Oats | 4 | 2 | 4 | 4 | 3 | 3 | 4 | 3 | 3 | 2 | 0 | 0 | 2 | 1 | 1 | 0 | 0 | 0 | 0 | 0 |
| Alfalfa | 4 | 4 | 4 | 4 | 4 | 4 | 4 | 4 | 4 | 4 | 2 | 2 | 1 | 1 | 4 | 4 | 4 | 4 | 3 | 2 |
| Cotton | 0 | 0 | 2 | 0 | 1 | 0 | 0 | 0 | 1 | 0 | 0 | 0 | 1 | 0 | 1 | 0 | 3 | 3 | 4 | 4 |
| Peanut | 2 | 0 | 0 | 0 | 0 | 0 | 0 | 0 | 0 | 0 | 0 | 0 | 0 | 0 | 0 | 0 | 2 | 1 | 1 | 0 |
| Soybean | 1 | 0 | 1 | 0 | 1 | 0 | 0 | 0 | 1 | 0 | 0 | 0 | 0 | 0 | 0 | 0 | 2 | 2 | 1 | 1 |
| Sugar Beets | 4 | 4 | 2 | 0 | 2 | 1 | 4 | 1 | 4 | 2 | 0 | 0 | 2 | 0 | 2 | 4 | 2 | 0 | 2 | 0 |
| Tomato | 4 | 1 | 3 | 0 | 1 | 0 | 1 | 0 | 2 | 0 | 0 | 0 | 2 | 0 | 3 | 4 | 2 | 1 | 2 | 1 |
| Corn | 3 | 2 | 4 | 3 | 4 | 4 | 4 | 3 | 3 | 2 | 1 | 0 | 0 | 0 | 3 | 0 | 3 | 1 | 3 | 1 |
| Grain Sorghum | 4 | 4 | 4 | 4 | 4 | 4 | 4 | 4 | 4 | 4 | 4 | 3 | 0 | 0 | 4 | 2 | 4 | 3 | 4 | 3 |
| Rice | 4 | 2 | 4 | 1 | 2 | 1 | 3 | 1 | 2 | 1 | 0 | 0 | 2 | 0 | 1 | 0 | 2 | 0 | 1 | 0 |
| Wheat | 3 | 2 | 2 | 1 | 3 | 2 | 3 | 2 | 2 | 2 | 0 | 0 | 0 | 0 | 2 | 1 | 0 | 0 | 1 | 0 | c. Use of the Compounds as Insecticides and Miticides

Laboratory procedures which may be used to demonstrate the use of the compounds as insecticides and miticides are described below.

Method for Mites, Aphids, Bean Beetles and Army Worms

Three 5 oz. paper cups containing Henderson dwarf lima bean plants and one 5 oz. paper cup containing Orange Gem nasturiums, all growing in vermiculite, are placed on a turntable and sprayed to thorough wetness with 25 ml of a solution of the candidate chemical at the appropriate concentration. Nasturtiums were already infested with 50–100 bean aphids (BA) (*Aphis fabae*). A bean plant in one paper cup was already infested with 50–100 two-spotted mites (TSM) (*Tetranychus bimaculatus*). Leaves from the two remaining bean plants are removed following spraying and placed in disposable petri dishes with 5 southern armyworm (SA) larvae (*Spodoptera efridania*) in one petri dish, and 5 Mexican bean beetle (MBE) larvae (*Epilachna varivestis*) in the other petri dish. The rating is done approximately 48 hours after spraying as follows:

| | | BA | TSM |
| --- | --- | --- | --- |
| 0 | — | E = none dead | 0 = no dead adults |
| 1 | 1–25 | D = 1–25% dead | 1 = 1–25% dead adults |
| 2 | 26–50 | C = 26–50% dead | 2 = 26–50% dead adults |
| 3 | 51–75 | B = 51–75% dead | 3 = 51–75% dead adults |

-continued

| | | |
|---|---|---|
| 4 76-99+ | A = 76-99% dead | 4 = 76-99% dead adults |
| 5 100% | | 5 = 100% dead adults | humidity were the same in all tests. Atmospheric pressure was not controlled.

Test results obtained at various concentrations of active chemical are tabulated below.

RESULTS OF INSECTICIDAL AND MITICIDAL USE

| Compound No. | Species | 500 | 250 | 125 | 100 | 62 | 50 | 31 | 25 | 15 | 12 | 8 | 6 | 4 | 3 | 2 |
|---|---|---|---|---|---|---|---|---|---|---|---|---|---|---|---|---|
| 1 | MBB | 5 | 5 | 3 | | 5 | 2 | 0 | | | | | | | | |
|   | SA | 0 | | | | | | | | | | | | | | |
|   | BA | 1 | | | | | | | | | | | | | | |
|   | TSM | 5 | 4 | 3 | | 2 | 0 | | | | | | | | | |
|   | SCR | | | | 0 | | | | | | | | | | | |
| 2 | MBB | 5 | 5 | 5 | | 5 | 5 | 5 | | 5 | | | 3 | | 0 | |
|   | SA | 5 | 5 | 1 | | 0 | 0 | | | | | | | | | |
|   | BA | 4 | 1 | 0 | | 0 | | | | | | | | | | |
|   | TSM | 2 | 3 | 0 | | 0 | | | | | | | | | | |
|   | SCR | | | | 0 | | | | | | | | | | | |
| 6 | MBB | 5 | 5 | 5 | | 5 | 4 | 2 | | 0 | | 0 | | | | |
|   | SA | 5 | 0 | 0 | | | | | | | | | | | | |
|   | BA | 5 | 4 | 3 | | 1 | 0 | | | | | | | | | |
|   | TSM | 5 | 5 | 5 | | 5 | 3 | 2 | | | | | | | | |
|   | SCR | | | | 0 | | | | | | | | | | | |
| 7 | MBB | 5 | 5 | 5 | | 5 | 1 | 0 | | 0 | | | | | | |
|   | SA | 0 | | | | | | | | | | | | | | |
|   | BA | 2 | | | | | | | | | | | | | | |
|   | TSM | 5 | 1 | 1 | | 0 | 0 | | | | | | | | | |
|   | SCR | | | | 0 | | | | | | | | | | | |
| 9 | MBB | 5 | 5 | 5 | | 5 | 5 | 5 | | 5 | | | 3 | | 0 | |
|   | SA | 5 | 5 | 5 | | 5 | 2 | 0 | | | | | | | | |
|   | BA | 4 | 3 | 2 | | 0 | 0 | | | | | | | | | |
|   | TSM | 4 | 4 | 2 | | 0 | 0 | | | | | | | | | |
|   | SCR | | | | 0 | | | | | | | | | | | |
| 10 | MBB | 5 | 5 | 5 | | 5 | 5 | 2 | | 0 | | 0 | | | | |
|   | SA | 4 | 0 | 0 | | | | | | | | | | | | |
|   | BA | 4 | 4 | 3 | | 0 | 0 | | | | | | | | | |
|   | TSM | 5 | 4 | 1 | | 0 | 0 | | | | | | | | | |
|   | SCR | | | | | | | 5 | | 5 | | 5 | | 4 | | |
| 11 | MBB | 5 | 5 | 5 | | 5 | 5 | 2 | | | | | | | | |
|   | SA | 5 | 0 | 0 | | 0 | | | | | | | | | | |
|   | BA | 3 | 1 | 0 | | 0 | | | | | | | | | | |
|   | TSM | 5 | 5 | 4 | | 4 | 2 | 2 | | 2 | | 0 | | | | |
|   | SCR | | | | 3 | | | | | | | | | | | |

| MBA | | | SA | |
|---|---|---|---|---|
| 0 | — | larvae dead | 0 = no larvae dead | |
| 1 | 1-25% | larvae dead | 1 = 1-25% larvae dead | |
| 2 | 26-50 | larvae dead | 2 = 26-50% larvae dead | |
| 3 | 51-75 | larvae dead | 3 = 51-75% larvae dead | |
| 4 | 76-99+ | larvae dead | 4 = 76-99% larvae dead | |
| 5 | 100% | | 5 = 100% larvae dead | |

Method for Southern Corn Rootworm (SCR)

Three 5 oz. paper cups planted each with one kernel of DeKalk XL-361 corn are treated two days after planting with 10 ml of a 125 ppm solution of the candidate compound. Promising compounds are tested at lower concentrations. The experiment is a 4×5 factorial in a randomized complete block design with three replications. The tests are evaluated nine days after treatment. The roots are inspected under a dissecting microscope and rated as follows:

| SCR Rating | % Root Feeding Damage |
|---|---|
| 5 | 0 |
| 4 | 1-25 |
| 3 | 26-50 |
| 2 | 51-75 |
| 1 | 76-99 |
| 0 | 100 |

So as to obtain more meaningful results, all tests were performed at the same time of day, whenever possible, usually in the forenoon. Temperature, illumination and humidity were the same in all tests. Atmospheric pressure was not controlled.

Some of the compounds disclosed above have been shown to have unusual utility as agricultural pesticides in certain specific problem situations, as described below.

Compound No. 3 is generally safe to use on soybeans for pre-emergent weed control. The compound is also an effective post-emergent herbicide and has given good control of weeds, particularly noxious grasses, when applied at 1 lb. per acre in fields of growing soybeans in the first trifoliate leaf stage. This herbicide has been found to be particularly suited to post-planting application in soybean fields at the time when cracks are forming along the planted rows, indicating that the soybean plants are about to emerge. Post-planting application kills weeds which have emerged subsequent to planting and also prevents the emergence of other weeds, so that the soybean plants are free of substantial competition from weeds during the early stages of growth. Pre-emergent or post-planting application of the compound is preferably made at a rate of from three-fourths to 2 lb. per acre (0.84 to 2.24 kg. per hectare), with the use of an inert diluent to obtain uniform distribution. Spray application of the compound in an aqueous dispersion is the preferred method.

Compound No. 3 is also useful in fall-planted wheat to combat cheat (*Bromus secalinus* L.). Preferably, the compound is applied pre-emergently at a rate of at least 1 lb. per acre, (1.12 kg. per hectare).

Compound No. 2 possesses an advantageous combination of properties which make this substance particularly useful as a pre-emergent herbicide and insecticide for use in rice fields to combat both weeds and soil-borne larvae of insect pests such as the rice water weevil. The compound is preferably applied in the manner conventionally employed for pre-emergent herbicides at an application rate of at least one pound per acre, preferably two to five pounds per acre when both weed control and insect control are desired. Compound No. 2 also gives good weed control in soybean fields when applied pre-emergently at a rate of from 1 to 3 lb. per acre, (1.12 to 3.36 Kg. per hectare).

Compound No. 10, unlike compound No. 2, which is highly toxic to corn, may be used in corn fields for combined pre-emergent control of weeds and control of soil-borne insect larvae such as corn rootworm. The compound is preferably applied to the soil at corn planting time, conveniently by spraying into the open furrow, before or after dropping the seed and prior to covering the seed with soil, at an application rate of at least one pound per acre, (1.12 kg. per hectare) on the sprayed area.

It is understood, according to present practice that combating weeds and insects means killing substantial numbers of these pests, sufficient to have a beneficial effect on the crop in which the pesticide is used. Complete kill or elimination of the pests is not necessary or desirable because an attempt to accomplish this usually results in development of pesticide-resistant strains of insects and weeds. Likewise, when the control of weeds and insects is referred to, this means the limiting of pest populations sufficiently so as to benefit the crop. Absolute control, or complete elimination of the pests from a relatively small geographical area is uneconomical and does not prevent the often disastrous resurgence of pest populations during future growing seasons.

It is also understood that an effective amount of chemical is a sufficient amount to achieve a beneficial effect and is usually substantially less than the preferred rate of application, in which the cost of the method is balanced against the increase in value of the crop for maximum overall economic benefit. There may be specific situations in which it is desirable to use considerably more than an effective or a preferred amount of pesticide. An example of such a situation is an integrated pest control program in which many farmers in a very large area are engaged in an effort to substantially eliminate a pest from the entire region. Ordinarily, however, the use of excessive amounts is not economically beneficial.

I claim:
1. O,O-Diethyl S-(N-isopropyl-3,4-dichlorophenylcarbamoylmethyl)dithiophosphate.
2. O,O-Diethyl S-(N-isopropyl-4-nitrophenylcarbamoylmethyl)dithiophosphate.

* * * * *